United States Patent [19]

Petchul et al.

[11] Patent Number: 5,575,948
[45] Date of Patent: *Nov. 19, 1996

[54] PROCESS AND COMPOSITION FOR MICROEMULSION GEL HAVING BLEACHING AND ANTISEPTIC PROPERTIES

[75] Inventors: John Petchul, 2221 Windy Hill La., Lake Orion, Mich. 48363; Rosemary Gaudreault, Park Ridge, Ill.

[73] Assignee: John Petchul, Lake Orion, Mich.

[*] Notice: The term of this patent shall not extend beyond the expiration date of Pat. No. 5,336,432.

[21] Appl. No.: 287,087

[22] Filed: Aug. 8, 1994

Related U.S. Application Data

[63] Continuation-in-part of Ser. No. 825,560, Jan. 24, 1992, Pat. No. 5,336,432.

[51] Int. Cl.$^6$ .................... C01B 15/01; B01J 13/00; A61K 7/135
[52] U.S. Cl. ................ 252/186.28; 252/186.43; 252/309; 252/312; 252/315.1; 424/62; 514/944
[58] Field of Search .................. 252/309, 312, 252/186.27, 186.28, 186.29, 186.43, 315.1, 315.2; 424/62, DIG. 3, 53, 613; 514/941, 944

[56] References Cited

U.S. PATENT DOCUMENTS

| | | | |
|---|---|---|---|
| 2,886,532 | 5/1959 | Richmond et al. | 252/309 |
| 3,114,720 | 12/1963 | Nixon | 423/625 X |
| 3,996,341 | 12/1976 | Lee | 423/589 X |
| 4,010,872 | 3/1977 | Lozano et al. | 424/62 X |
| 4,146,499 | 3/1979 | Rosano | 252/312 |
| 4,184,978 | 1/1980 | France et al. | 252/309 |
| 4,351,820 | 9/1982 | Thirion | 423/588 X |
| 4,472,291 | 9/1984 | Rosano | 252/186.28 |
| 4,496,473 | 1/1985 | Sanderson | 424/62 X |
| 4,835,002 | 5/1989 | Wolf et al. | 426/602 |
| 4,927,627 | 5/1990 | Schrader et al. | 252/186.28 |
| 4,934,457 | 6/1990 | Wallender | 252/186.28 X |
| 5,017,354 | 5/1991 | Simms et al. | 423/338 |
| 5,076,954 | 12/1991 | Loth et al. | 252/122 |
| 5,102,655 | 4/1992 | Yoshihara et al. | 424/62 |
| 5,271,860 | 12/1993 | Schwadtke et al. | 252/96 |
| 5,419,847 | 5/1995 | Showell et al. | 252/100 |
| 5,492,540 | 2/1996 | Leifheit et al. | 252/186.43 |

OTHER PUBLICATIONS

The Merck Index, (Merck & Co., Inc. 1983, Rahway, N.J.) pp. 1130–1131.

H. Bennett, *Practicle Emulsions*, (Chemical Publishing Co., Inc., Brooklyn, N.Y., 1943) p. 272.

Kevin Gallagher, "Microemulsion Gels: A Formulators Guide", HAPPI/Feb. 1993 (Croda, Inc.) pp. 58, 60, 62, and 64. Feb. 1993.

*Primary Examiner*—Richard D. Lovering
*Assistant Examiner*—Daniel S. Metzmaier
*Attorney, Agent, or Firm*—Gifford, Krass, Groh, Sprinkle, Patmore, Anderson & Citkowski, P.C.

[57] ABSTRACT

A microemulsion gel having antiseptic and bleaching properties is prepared from the combination of a water phase comprising water and propylene glycol with an oil phase generally comprising one or more surfactants, an emollient, and an oil. In its preferred embodiment, the oil phase comprises a polyethylene glycol ether of isocetyl alcohol, preferably Isoceteth-20, a polyethylene glycol ether of oleyl alcohol, preferably Oleth-2, and a polypropylene glycol ether of stearyl alcohol, preferably PPG-15 stearyl ether. The water phase optionally includes sorbitol and the oil of the oil phase may be mineral oil. The water and oil phases are heated independently then combined and mixed. Hydrogen peroxide is subsequently added to the composition, and the combination is cooled and allowed to stand until a gel is formed. A fragrance may be added as desired.

6 Claims, No Drawings

PROCESS AND COMPOSITION FOR MICROEMULSION GEL HAVING BLEACHING AND ANTISEPTIC PROPERTIES

CROSS-REFERENCE TO RELATED APPLICATIONS

This is a continuation-in-part of U.S. patent application Ser. No. 07/825,560, filed Jan. 24, 1992, U.S. Pat. No. 5,336,432 entitled PROCESS AND COMPOSITION FOR MICROEMULSION GEL HAVING BLEACHING AND ANTISEPTIC PROPERTIES.

BACKGROUND OF THE INVENTION

I. Field of the Invention

The present invention relates to a process and composition for a microemulsion gel having bleaching and antiseptic properties. More particularly, the present invention comprises the mixture of a water phase, an oil phase and hydrogen peroxide. The water phase includes propylene glycol and water. The oil phase includes one or more surfactants, an emollient, and an oil.

II. Description of the Relevant Art

Hydrogen peroxide has long been used as an antiseptic and a bleach. When used for these purposes, the hydrogen-oxygen compound is generally diluted to 3 to 6 percent by weight.

The strong oxidizing properties of hydrogen peroxide render it an excellent bleaching agent in both industrial and consumer applications. When employed in industry, hydrogen peroxide is often used in the bleaching (and deodorizing) of textiles, wood and paper pulp, fur, and food stuffs including flour, oils, fats, and sugar. By reacting chemically with the discoloring components of the treated materials, these components are oxidized or reduced to a colorless form or to a form which is soluble and can be removed by subsequent washing.

Consumer salon and home applications of hydrogen peroxide as a bleach are most often directed to the bleaching or decoloring of human hair. When used in this capacity, hydrogen peroxide is typically combined with other chemicals called bleaching assistants to assume more uniform penetration of the hair by the bleach and more complete control of the process.

The consumer use of known hydrogen peroxide-containing compounds provided for use as decolorizers of human hair is constrained by several undesirable characteristics, the main problem being a general one of control. Hydrogen peroxide is itself a thick, syrupy liquid that, along with the bleaching assistants, is sold as a solution in water. The resulting "oil bleach", as it is called by beauticians, tends to be overinvasive and easily contacts the scalp, skin and eyes. Because it is a strong irritant, the unrestricted distribution of hydrogen peroxide can cause severe burning.

Hydrogen peroxide also has valuable application as an antiseptic. As such it is often applied to humans or animals to retard or stop the growth of microorganisms considered harmful. Hydrogen peroxide is viscous in pure form, but is generally diluted to 3 percent by weight with water when used as an antiseptic. The resulting solution is pervasive when applied as an antiseptic and tends to wander out of control. This characteristic contributes to wasteful excess in application.

Known methods of disinfecting skin and bleaching human hair have failed to overcome the main problems of product waste and lack of control over the distribution of hydrogen peroxide solutions.

SUMMARY OF THE PRESENT INVENTION

The present invention involves the preparation of a hydrogen peroxide-containing microemulsion gel that overcomes the principal problem of known bleaching and antiseptic solutions by allowing the user the ability to control dispersion of the compound.

The microemulsion gel of the present invention is prepared from the combination of two independent phases, one being of a water phase and the other an oil phase. The phases are each heated then commingled. Hydrogen peroxide is subsequently added, and the resulting solution is mixed and allowed to cool to a preselected temperature. The cooled solution is then allowed to stand until a microemulsion gel is formed.

The principal advantage of the present invention is that its colloidal nature allows the restriction by the user to selected areas of the body when used as an antiseptic and in the hair when used as a bleach for such specific applications as "streaking" and "frosting" while at the same time preventing the composition from wandering. Accordingly, the present invention overcomes problems of known antiseptic and hair bleaching solutions and methods.

Other objects and details of the present invention will become apparent from the following detailed description.

DETAILED DESCRIPTION OF THE PREFERRED EMBODIMENTS OF THE PRESENT INVENTION

The composition of the present invention includes as its basic components an oil phase and a water phase. Each phase is prepared independently of the other.

The oil phase is a product of the commingling of one or more surfactants, an emollient, and an oil. More particularly, the oil phase components include polyethylene glycol ethers of oleyl alcohol, polyethylene diesters of oleic acid, polyethylene glycol esters of any fatty acid, or a polyethylene glycol derivative of lanolin or oil. Specific components include a polyethylene glycol ether of isocetyl alcohol, preferably Isoceteth-20, a polyethylene glycol ether of oleyl alcohol, preferably Oleth-2, and a polypropylene glycol ether of stearyl alcohol, preferably PPG-15 stearyl ether. Other possible substitutions include PEG-25 hydrogenated castor oil, Oleth-5, Oleth-10, Oleth-20 and PEG-20 hydrogenated lanolin.

In its preferred embodiment, the oil phase results from the use of Isoceteth-20 (between 1.0 and 35.0 percent by weight), Oleth-2 (between 0.5 and 10.0 percent by weight), and PPG-15 stearyl ether (between 0.5 and 10.0 percent by weight). Stearyl ether is not soluble in water and is frequently used in perfumery and cosmetics. Up to between 1.5 and 8.0 percent by weight of mineral oil may be added to the oil phase to adjust consistency.

The water phase is the product of the commingling of propylene glycol (between 0.5 and 8.0 percent by weight) and water (as much as necessary to provide desired consistency and solubility). Propylene glycol, which is miscible with the water component of this phase and which is often found in cleansing creams and suntan lotions, functions in the present invention as an emulsifier to assist in the stabilizing of the oil phase with the water phase which are ordinarily immiscible. Up to between 1.0 and 12.0 percent by weight of sorbitol may also be included in the water phase. Used as a moisture-conditioner to provide a desired texture and conditioning quality, sorbitol is soluble in both the water and the propylene glycol components of the water phase.

Once the components of the two phases are established, each phase is warmed to between 60° C. and 85° C. to improve solubility. The heated water phase is subsequently added to the heated oil phase. After addition, the phases are mixed together by stirring at a gradually increased rate of speed. The mixing process is thereafter slowed following a preselected time and the solution is allowed to cool to a preselected temperature of preferably 25° centigrade. It is important to understand that the speed and length of the mixing process may be varied according to the temperatures of the two phases as may be understood by one skilled in the art.

Hydrogen peroxide (between 2.5 and 35.0 percent by weight) is then introduced into the mixture after it cools. Phosphoric acid is also introduced at this time as required to adjust the pH of the mixture to approximately 3.4 (±0.1), although the pH range may be as broad as 3.0 to 5.0.

The mixing is continued for a preselected time and is then stopped. A suspension is allowed to form in the mixture resulting in the setting up of a transparent microemulsion gel. With some variation in the amounts of surfactants and oils as components in the present invention, a creme or paste product may be produced.

The gel product may be used in this form in the bleaching of human hair. Fragrances may be added as desired.

In an alternate embodiment of the present invention, a lower concentration of hydrogen peroxide may be used according to the formulation set forth above to provide a gel usable as an antiseptic.

The invention will be better understood from a consideration of the following example. All percentages are based upon weight.

EXAMPLE

Process For Producing Microemulsion Gel

Having Bleaching Characteristics

As discussed, the oil phase includes one or more surfactants, an emollient, and an oil. According to the present example, the oil phase was established by the commingling of 22.39 percent Isoceteth-20, 3.68 percent mineral oil, 3.68 percent Oleth-2, and 2.14 percent PPG-15 stearyl ether. A water phase was established by the commingling of 3.33 percent propylene glycol, 4.60 percent sorbitol and the balance water. Each phase was independently heated to between 75° C. and 78° C. After achieving the desired temperatures, the water phase was added to the oil phase, and mixing of the two phases began. The speed of mixing was gradually increased. Mixing continued for a period of twenty minutes, afterwhich the speed of mixing was decreased and the mixture was allowed to cool to between 25° C. and 30° C. Once the temperature of the mixture dropped to the preferred level of 25° C., 3.37 percent hydrogen peroxide was added while mixing was continued. The pH value of the mixture was adjusted to 3.4 (±0.1) by the addition of phosphoric acid. Mixing continued thereafter for a period of 10 minutes and was then halted. The mixture was allowed to stand and a microemulsion gel was built after 20 minutes.

The invention being thus described, it will be obvious that the same may be varied in many ways. Such variations are not to be regarded as a departure from the spirit and scope of the invention, and all such modifications are intended to be included within the scope of the following claims.

What is claimed is:

1. A composition of matter comprising:

a water phase consisting essentially of between 8.0 and 64.0 percent by weight water and between 0.5 and 8.0 percent by weight propylene glycol;

an oil phase consisting essentially of between 1.08 and 40.0 percent by weight of a polyethylene glycol ether of isocetyl alcohol, between 0.5 and 12.0 percent by weight of a polyethylene glycol ether of oleyl alcohol, and between 1.5 and 10.0 percent by weight of a polypropylene glycol ether of steryl alcohol; and between 2.5 and 35.0 percent by weight hydrogen peroxide;

wherein said composition is a microemulsion gel.

2. The composition of claim 1, wherein said oil phase comprises between 3.5 and 62.0 percent by weight of said polyethylene glycol ethers and said polypropylene glycol ethers.

3. The composition of claim 1, wherein said water phase further includes up to about 12.0 percent by weight sorbitol.

4. The composition of claim 1, wherein said oil phase further includes up to about 8.0 percent by weight mineral oil.

5. The composition of claim 1, wherein said composition further includes phosphoric acid in an amount sufficient to adjust the pH of said composition to a balance of about 3.4.

6. The composition of claim 1, wherein said composition is transparent.

* * * * *